(12) United States Patent
Baynham

(10) Patent No.: US 10,194,967 B2
(45) Date of Patent: Feb. 5, 2019

(54) MINIMALLY INVASIVE SPINE SURGERY INSTRUMENTS: GUIDE WIRE HANDLE WITH A GUIDE WIRE LOCKING MECHANISM

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 0 days.

(21) Appl. No.: 14/033,214

(22) Filed: Sep. 20, 2013

(65) Prior Publication Data

US 2014/0094822 A1   Apr. 3, 2014

Related U.S. Application Data

(60) Provisional application No. 61/704,132, filed on Sep. 21, 2012.

(51) Int. Cl.
*A61B 17/88* (2006.01)
*A61B 17/70* (2006.01)

(52) U.S. Cl.
CPC ...... *A61B 17/8861* (2013.01); *A61B 17/7002* (2013.01); *A61B 17/7004* (2013.01); *A61B 17/7083* (2013.01)

(58) Field of Classification Search
CPC .................................................. A61B 17/8861
USPC ........................................ 606/103, 148, 104
See application file for complete search history.

(56) References Cited

U.S. PATENT DOCUMENTS

| | | | |
|---|---|---|---|
| 5,152,749 A | 10/1992 | Giesy et al. | |
| 5,250,035 A * | 10/1993 | Smith et al. | 604/168.01 |
| 5,271,415 A | 12/1993 | Foerster et al. | |
| 5,531,699 A * | 7/1996 | Tomba et al. | 604/170.02 |
| 5,562,683 A * | 10/1996 | Chan | 606/139 |
| 6,423,080 B1 * | 7/2002 | Gellman et al. | 606/148 |
| 6,740,098 B2 * | 5/2004 | Abrams et al. | 606/148 |
| 6,746,483 B1 * | 6/2004 | Bojarski et al. | 623/13.14 |
| 6,827,722 B1 * | 12/2004 | Schoenefeld | A61B 17/1622 606/104 |
| 7,207,995 B1 * | 4/2007 | Vandewalle | A61B 17/8875 606/104 |
| 8,202,293 B2 * | 6/2012 | Ellingwood et al. | 606/213 |
| 8,313,496 B2 * | 11/2012 | Sauer et al. | 606/139 |
| 8,394,102 B2 * | 3/2013 | Garabedian et al. | 606/86 A |
| 8,540,737 B2 * | 9/2013 | Chudik | 606/148 |
| 8,551,097 B2 * | 10/2013 | Schmitz et al. | 606/79 |
| 8,568,416 B2 | 10/2013 | Schmitz et al. | |
| 8,579,902 B2 * | 11/2013 | Bleich et al. | 606/79 |
| 8,585,704 B2 * | 11/2013 | Schmitz et al. | 606/79 |
| 8,613,745 B2 * | 12/2013 | Bleich | 606/79 |
| 8,623,025 B2 * | 1/2014 | Tan-Malecki et al. | 606/92 |
| 8,647,346 B2 * | 2/2014 | Bleich et al. | 606/82 |
| 8,652,138 B2 * | 2/2014 | Bleich et al. | 606/79 |
| 8,663,228 B2 * | 3/2014 | Schmitz et al. | 606/85 |
| 9,855,087 B2 * | 1/2018 | Divincenzo | A61B 17/8875 |
| 2003/0078601 A1 * | 4/2003 | Shikhman et al. | 606/148 |
| 2004/0215190 A1 * | 10/2004 | Nguyen et al. | 606/61 |

(Continued)

*Primary Examiner* — Jan Christopher Merene
(74) *Attorney, Agent, or Firm* — McHale & Slavin, P.A.

(57) ABSTRACT

Disclosed are various instruments and implants used in minimally invasive spine surgery. Disclosed is a cannulated probe, a guide wire handle; a guide wire handle having a locking mechanism, an all-in-one guide wire tool; a retractor flex rod passage; or a tab break tool.

3 Claims, 16 Drawing Sheets

(56) References Cited

U.S. PATENT DOCUMENTS

| | | | |
|---|---|---|---|
| 2005/0165419 A1* | 7/2005 | Sauer et al. | 606/148 |
| 2005/0240198 A1* | 10/2005 | Albertson et al. | 606/103 |
| 2006/0258951 A1* | 11/2006 | Bleich et al. | 600/546 |
| 2009/0069846 A1* | 3/2009 | Bull et al. | 606/228 |
| 2009/0138048 A1* | 5/2009 | Baccelli et al. | 606/263 |
| 2009/0275994 A1* | 11/2009 | Phan et al. | 606/86 A |
| 2009/0287227 A1* | 11/2009 | Newell et al. | 606/148 |
| 2010/0057091 A1* | 3/2010 | Oosterom | 606/103 |
| 2010/0087836 A1* | 4/2010 | Jaramillo et al. | 606/144 |
| 2010/0087872 A1* | 4/2010 | Morihara et al. | 606/300 |
| 2010/0298829 A1* | 11/2010 | Schaller et al. | 606/74 |
| 2011/0054537 A1* | 3/2011 | Miller | A61B 17/1655 606/279 |
| 2011/0077656 A1* | 3/2011 | Sand et al. | 606/96 |
| 2011/0087225 A1* | 4/2011 | Fritzinger | 606/53 |
| 2011/0087232 A1* | 4/2011 | Levatich | 606/94 |
| 2011/0245833 A1* | 10/2011 | Anderson | 606/80 |
| 2011/0319925 A1* | 12/2011 | Helgerson | A61B 17/3421 606/198 |
| 2012/0004665 A1* | 1/2012 | Defossez | A61B 17/8872 606/108 |
| 2012/0109129 A1* | 5/2012 | Bernstein | 606/74 |
| 2012/0179146 A1* | 7/2012 | Fan et al. | 606/1 |
| 2012/0184958 A1* | 7/2012 | Knuchel et al. | 606/59 |
| 2012/0265260 A1* | 10/2012 | Yamaguchi et al. | 606/86 R |
| 2012/0323280 A1* | 12/2012 | Chin et al. | 606/279 |
| 2013/0053851 A1* | 2/2013 | Schmitz et al. | 606/79 |
| 2013/0116736 A1* | 5/2013 | De Oliveira | 606/86 R |
| 2013/0165930 A1* | 6/2013 | Lehmann et al. | 606/54 |
| 2013/0184720 A1* | 7/2013 | Aldridge et al. | 606/148 |
| 2013/0261625 A1* | 10/2013 | Koch et al. | 606/74 |
| 2013/0274769 A1* | 10/2013 | Bonutti et al. | 606/148 |
| 2014/0276890 A1* | 9/2014 | Khosla et al. | 606/103 |
| 2014/0303625 A1* | 10/2014 | Sholev et al. | 606/80 |
| 2014/0364863 A1* | 12/2014 | Prien | 606/104 |
| 2015/0045795 A1* | 2/2015 | Sholev et al. | 606/79 |

\* cited by examiner

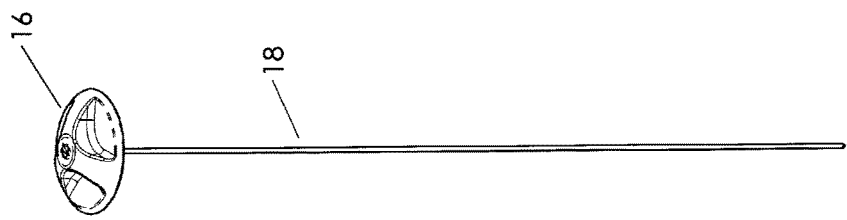
FIG. 4
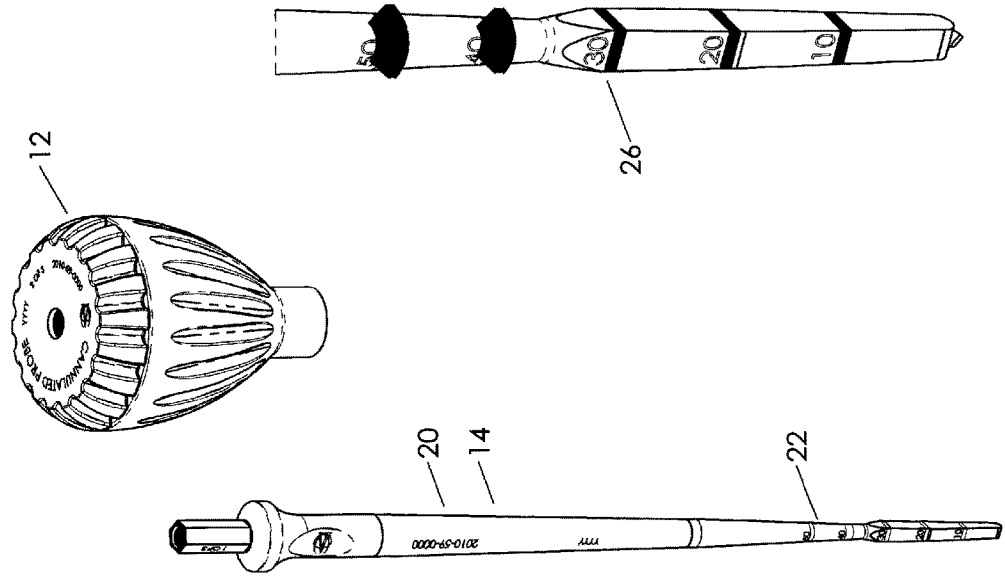
FIG. 3
FIG. 2
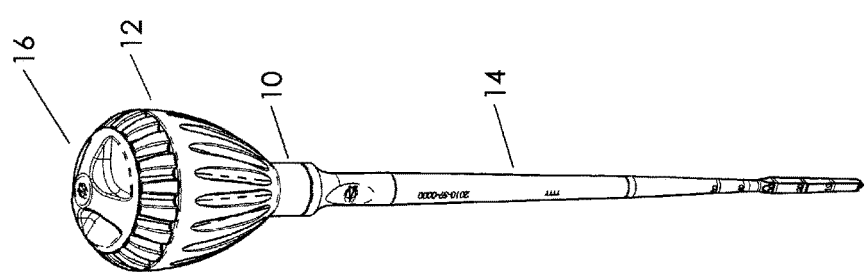
FIG. 1

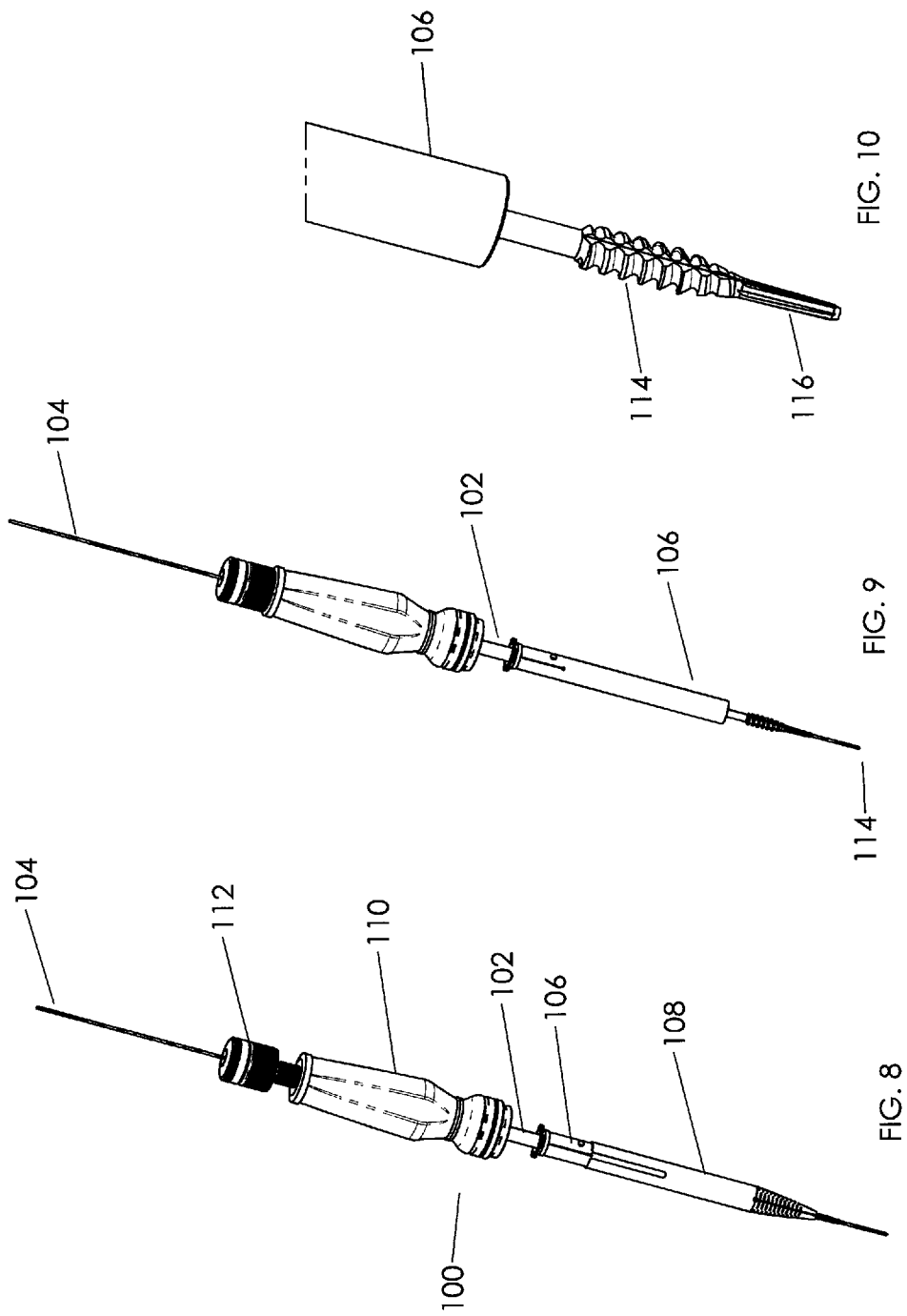

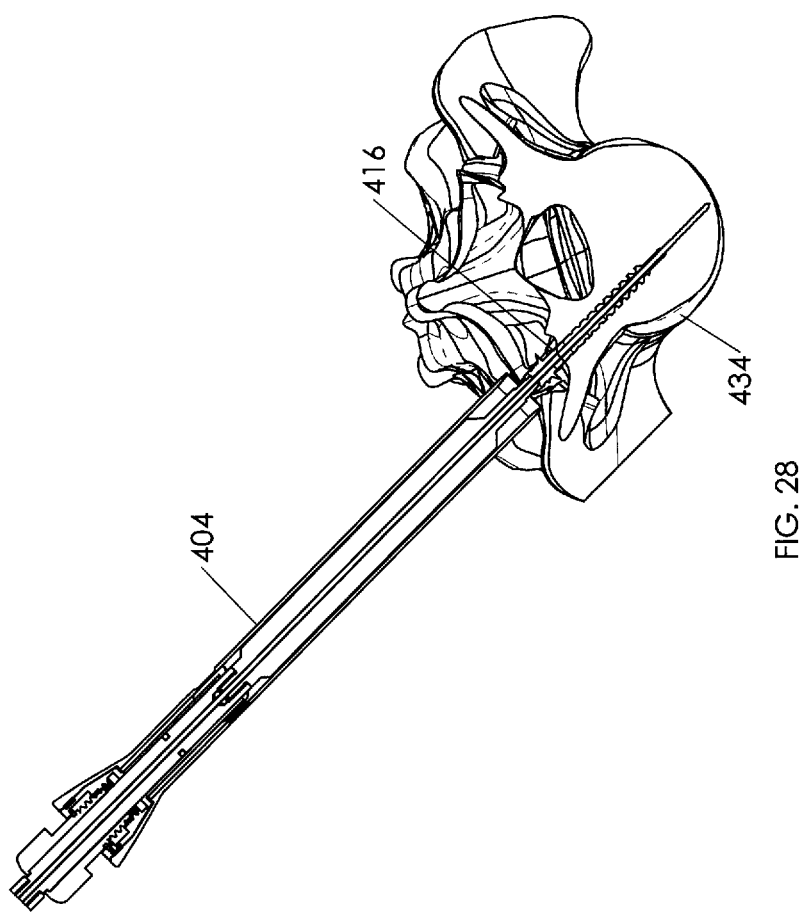

MINIMALLY INVASIVE SPINE SURGERY INSTRUMENTS: GUIDE WIRE HANDLE WITH A GUIDE WIRE LOCKING MECHANISM

CROSS REFERENCE TO RELATED APPLICATION

In accordance with 37 C.F.R. 1.76, a claim of priority is included in an Application Data Sheet filed concurrently herewith. Accordingly, the present invention claims priority to U.S. Provisional Patent Application No. 61/704,132, entitled "MINIMALLY INVASIVE SPINE SURGERY INSTRUMENTS", filed Sep. 21, 2012. The contents of which the above referenced application is incorporated herein by reference.

FIELD OF THE INVENTION

This invention relates to instruments and implants used to treat various problems of the spine.

DESCRIPTION OF THE PRIOR ART

Minimally invasive spine surgery can be used to effectively treat disorders of the spinal discs with minimal muscle related injury. In many procedures, a surgeon makes several small incisions (percutaneous) wherein a miniature camera (usually a laparoscope or endoscope) is placed so the surgeon can view the procedure as a magnified image on video monitors in the operating room. Specialized instruments are placed through the incisions to perform various procedures. Minimally invasive spine surgery may include: Spinal fusion such as on degenerative disks; deformity corrections, such as for scoliosis; repair of herniated disks; repair and stabilization of vertebral compression fractures and decompression of spinal tumors to name a few. In certain cases of degenerative discs, scoliosis, kyphosis, spinal column tumors, infection, fractures and herniated discs, minimally invasive techniques may speed recovery, minimize post-operative pain and improve the final outcome.

SUMMARY OF THE PRESENT INVENTION

The inventions disclosed are directed to various instruments and implants used in minimally invasive spine surgery. Disclosed is: a cannulated probe, a guide wire handle; guide wire handle having guide wire locking mechanism, an all-in-one guide wire tool; a retractor flex rod passage; a tab break tool; a modular screw head; a flange rod; and a perc rod inserter.

Objectives, advantages and benefits associated with these inventions will be apparent to those skilled in the art from the description and drawings which follow.

BRIEF DESCRIPTION OF THE DRAWINGS

FIG. 1 is a perspective view of a cannulated probe embodiment;

FIG. 2 is perspective view of the cannulated probe in FIG. 1 with the handle detached;

FIG. 3 is a perspective view of the cannulated probe in FIG. 1 stylus;

FIG. 4 is an enlarged view of the cannulated probe in FIG. 1 distal tip;

FIG. 8 is a perspective view of an all-in-one guide wire tool embodiment;

FIG. 9 is a perspective view of the guide wire tool in FIG. 8 depicting the protective sleeve without the flex cover;

FIG. 10 is a perspective view of the guide wire tool in FIG. 8 depicting the bone tap;

FIG. 28 illustrates an alternative view of the guide wire management system engaged with a vertebral body.

DETAILED DESCRIPTION OF THE INVENTION

Figure 5:
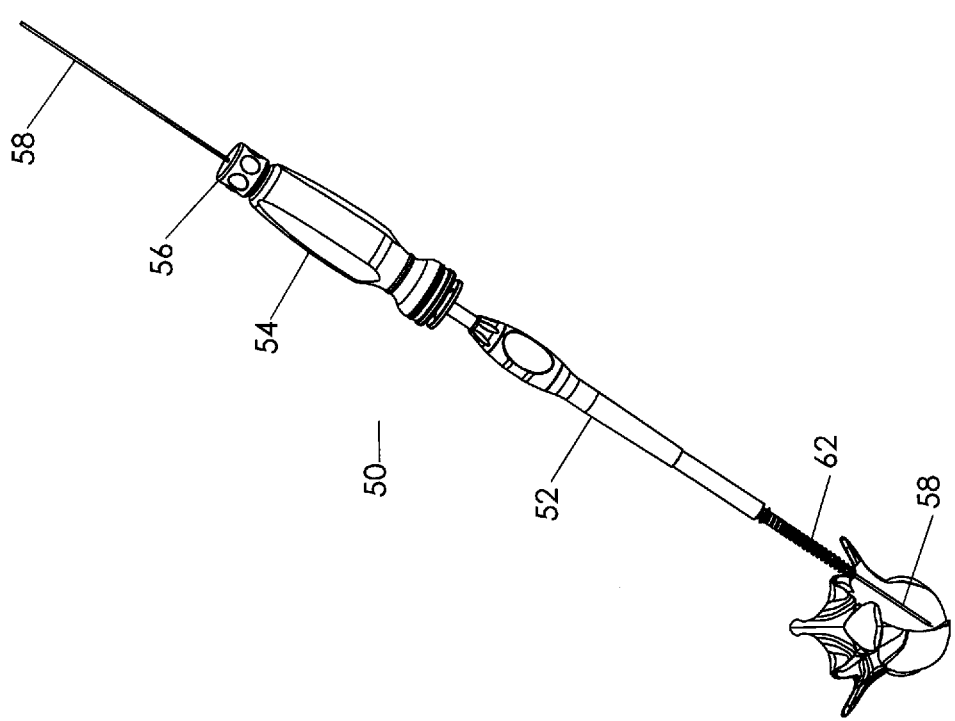
FIG. 5 is a perspective view of a guide wire embodiment.

Referring to FIGS. 1-4, set forth is a cannulated probe 10 having a handle 12, a shaft 14, stylus cap 16 and stylus 18. The shaft 14 has an upper section 20 made of a radiolucent material and a lower section 22 made of a radio opaque material. The lower section 22 including graduated markings 26. Unique to this invention is the ability to remove the handle 12 wherein an uninterrupted viewing of along the length of the shaft from above the now displaced handle is made possible. The handle made from a low cost material that would otherwise disrupt imaging. The stylus 18 can be reinserted into the shaft 14 without the handle. The radiolucent shaft with a radiopaque tip is unique and could be adapted to a variety of pedicle prep instruments including Jam shidi, awl, tap and so forth.

Figure 6:
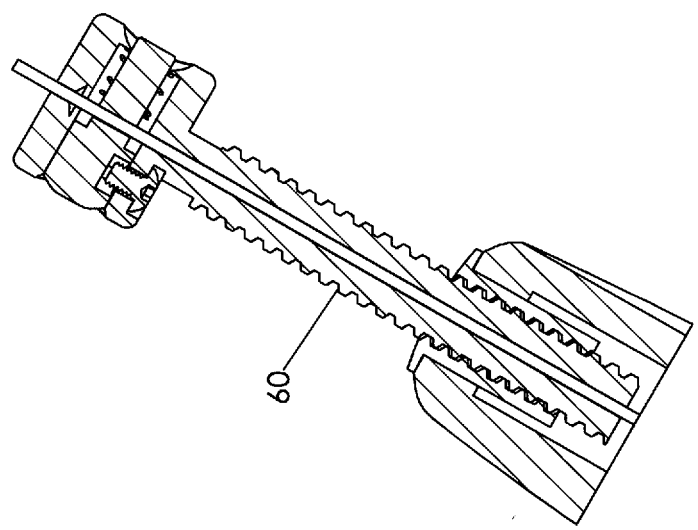
FIG. 6 is a cross sectional view of the guide wire handle in FIG. 5 in a raised position.
Figure 7:
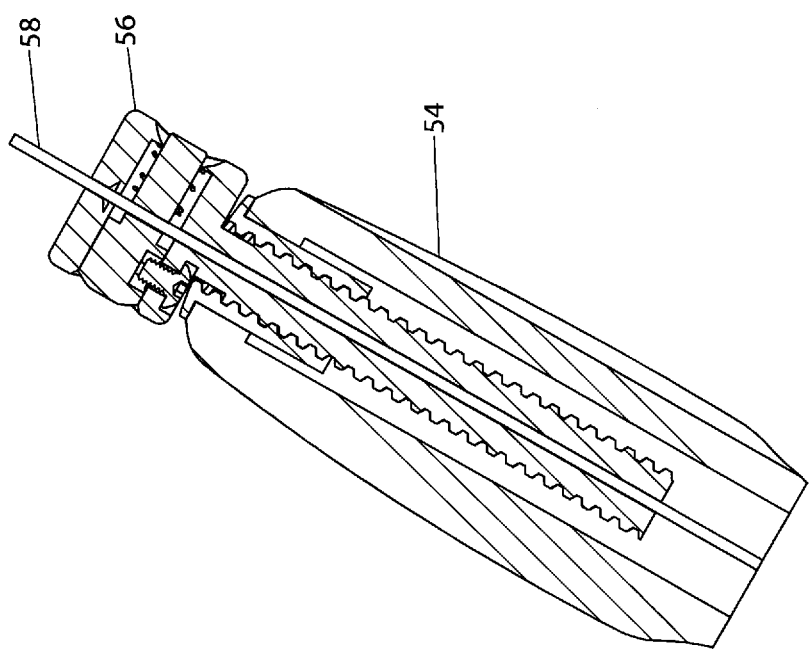
FIG. 7 is a cross sectional view of the guide wire handle in FIG. 5 in a lowered position.
Figure 14:
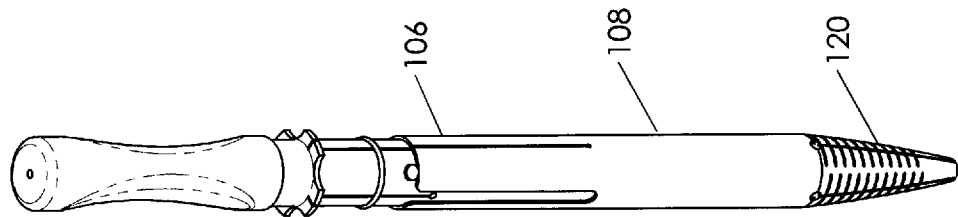
FIG. 14 is a perspective view of the guide wire tool in FIG. 8 depicting the assembly of the expandable dilator over the protective sleeve.
Figure 13:
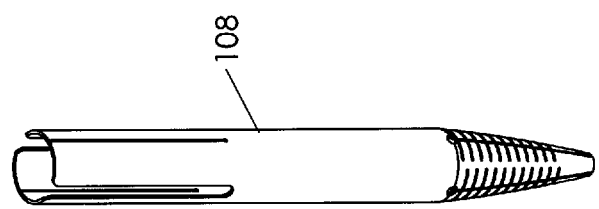
FIG. 13 is a perspective view of the guide wire tool in FIG. 8 depicting the expandable dilator.
Figure 12:
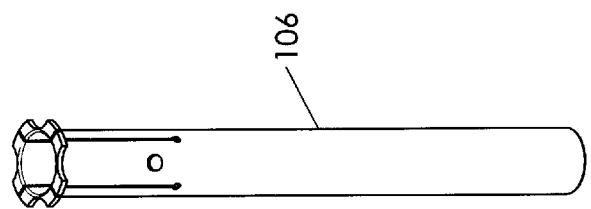
FIG. 12 is a perspective view of the guide wire tool in FIG. 8 depicting the protective sleeve.
Figure 11:
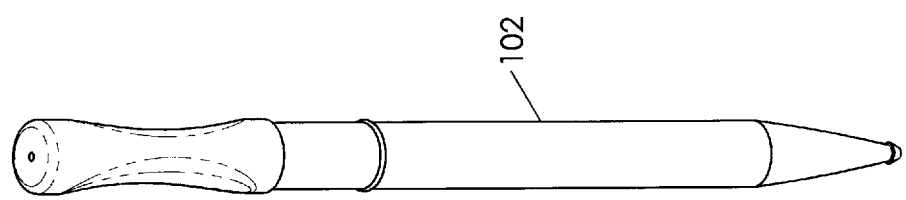
FIG. 11 is a perspective view of the guide wire tool in FIG. 8 depicting the guide housing.
Figure 15:
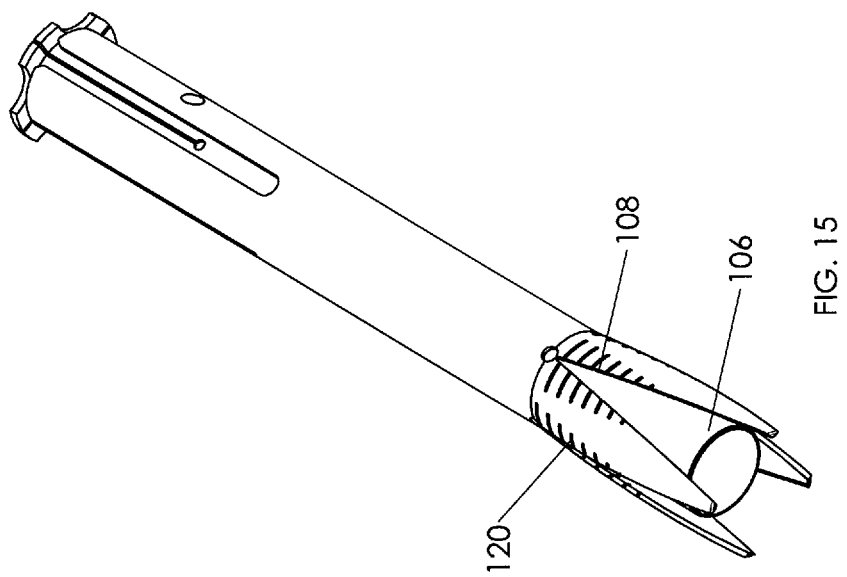
FIG. 15 is a pictorial view of the guide wire tool in FIG. 8 depicting the dilator sleeve in an expanded position.

FIGS. 5-7 depict a guide wire handle 50 having a shank 52, a handle 54 a guide wire capture handle 56 and a guide wire 58. The guide wire tool is used to control the position of a guide wire during insertion. The guide wire 58 can be held in the exact position by use of the guide wire capture handle 56. The capture handle 56 include a threaded rod 60 that engages an upper end of the handle 54 wherein rotation of the handle 54 in relation to the guide wire capture handle 56 allows rotation of the bone tap screw thread 62 have the exact same thread pitch movement. In this manner, rotation of the bone tap screw 62 is possible without movement of the guide wire 58. In the preferred embodiment, not shown, the guide wire capture handle may include a lever to allow for ease of engaging the guide wire. The screw depth can be measured from the guide wire handle. In another embodiment, the treaded rod and the tap screw thread are not matching threads but have a positioning shaft and an external engagement between the clamp on the wire and a fixed position, such as on the bed clamp. This device could be used during screw insertion and removal, tap insertion and removal to ensure the wire does not advance forward nor retreat back. The device could also be used to drive a wire forward in a controlled measurable manner.

Referring now to FIGS. 8-15, set forth is an all-in-one guide wire tool 100 formed from a shank 102, having a central passageway for a guide wire 104. The instrument allows for a single step dilation. The shank 102 includes a protective sleeve 106 with a expandable dilator 108. Handle 110 with guide handle 112. At the bottom of the shank 102 is a bone tap 114 and awl 116. The expandable dilator 108 having a serrated end 120 that expands upon the insertion of the sleeve 106 and retracts to the original position upon removal of the sleeve 106. The handle 110 may be used as a hammer or engaged with bone tap for ease of rotation. A unique feature to this embodiment being that in a single pass the surgeon is able to take the steps of an awl, jamshidi, guide wire placement and tap. The instrument uses the guide wire handle described above to ensure the guide wire position.

Figure 16:
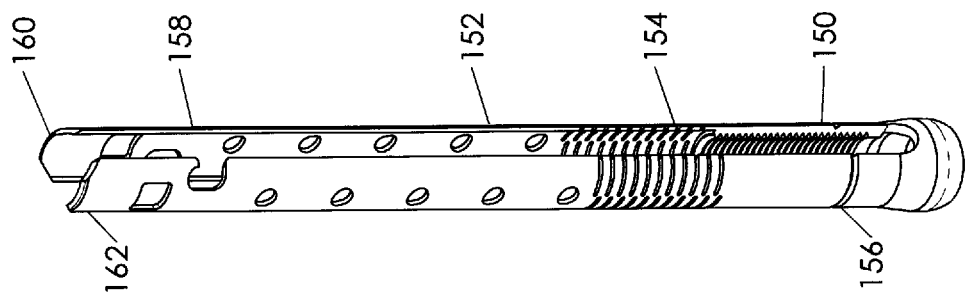
FIG. 16 is a perspective view of a retractor flex rod passage embodiment.

Referring now to FIG. 16 is a perspective view of a flex rod passage 150 screw-based device for use in minimally invasive surgery. The device is defined by a modular screw head 152 have a malleable zone 154 located above a break line 156. The malleable zone 154 allows the material to flex for ease of rod positioning. A non-ridged zone 158 is positioned above the malleable zone allowing blades 160 and 162 to be split apart thereby retracting of the soft tissue and allowing the surgeon to maintain a clear view of the operating site. In the preferred embodiment, the retractor is made from titanium, titanium alloy, surgical steel or the like material having properties that allow for a malleable zone that can be bent in a hinge like manner, and stay in the bent position until further movement by the surgeon. The material allows the blades to be placed in a position that allows the surgeon ease of access through the incision, the malleable zone 154 having score slots constructed and arranged to allow for bending of the blades which will stay in position until further moved. The malleable feature may also be used for soft tissue retraction during interbody placement or decompression work. In this scenario, the tabs would likely be bent in the same direction to provide a cephalad caudal retraction.

Figure 17:
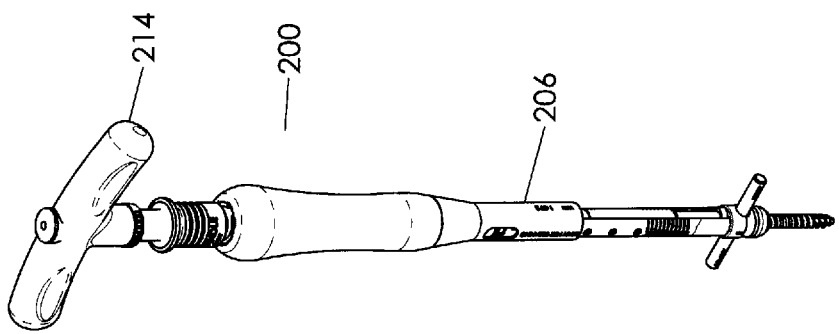
FIG. 17 is a perspective view of a tab break tool embodiment for a retractor.
Figure 19:
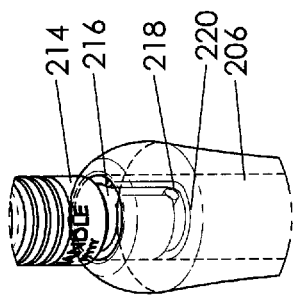
FIG. 19 is an enlarged view of the shaft lock used in the tab break tool illustrated in FIG. 17.
Figure 18:
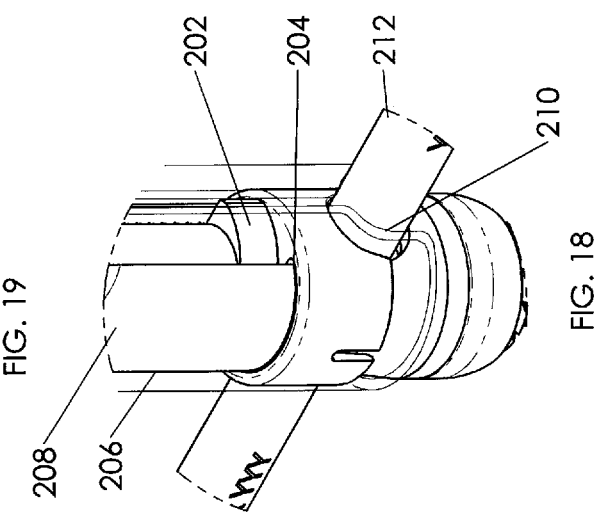
FIG. 18 is an enlarged view of the cam used in the tab break illustrated in FIG. 17.

Referring not to FIGS. 17-19, set forth is a perspective view of a tab break tool 200 for a retractor. The tool includes a cam 202 that is constructed and arranged to be placed adjacent to a break line 204 of a retractor shown in FIG. 16. An outer sleeve 206 is slidably positioned to the outside of the blades 208 of the retractor. Rotation of the cam 202 operates to shear the blades 208 along the break line 204. The outer sleeve 206 includes positioning edge 210 that partially encompasses a rod 212 to prevent rotation of the outer sleeve 206. Handle 214 is secured to a shaft 216 having engagement tab 218 positionable within slot 220 formed in the outer sleeve 206 for use in rotation.

Figure 20:
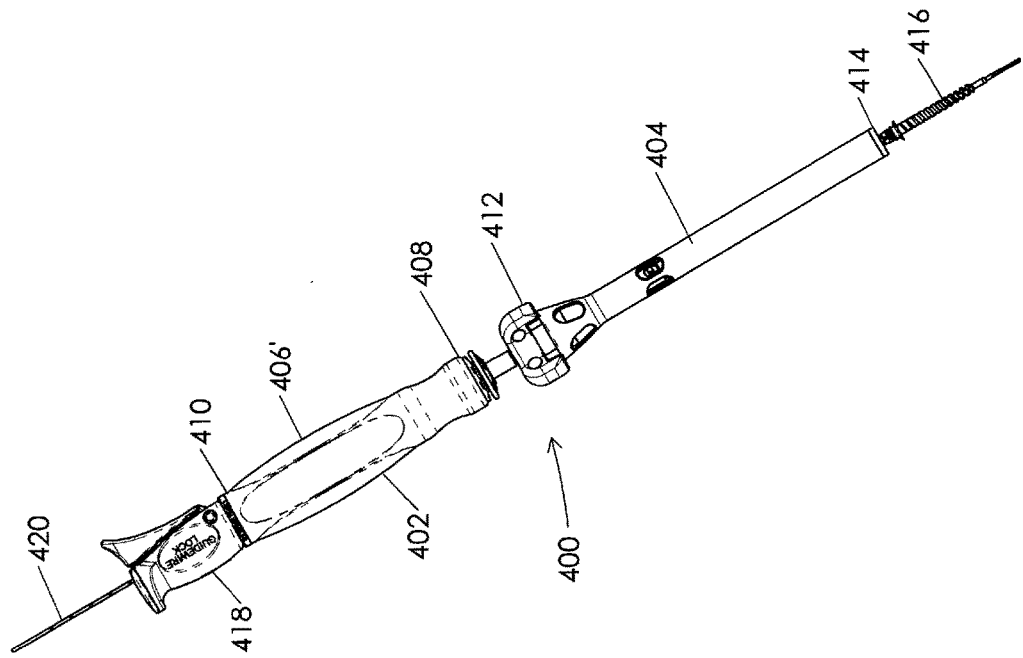
FIG. 20 is a an illustrative embodiment of a guide wire management system adapted to control the position of a guide wire during the insertion of various hole creating devices and/or screws using a locking mechanism.

Referring to FIG. 20, an alternative embodiment of the guide wire management system, similar to the embodiment described with handle 50 is shown. The guide wire management system, referred to generally as 400, is constructed to control the position of a guide wire during the insertion of various hole creating devices and or screws. The guide wire management system 400 includes a handle 402 and a cannulated body 404. The handle 402 includes a handle body 406, a first end 408 and a second opposing end 410. The first end 408 is adapted to secure or couple to the first end 412 of the cannulated body 404. A second end 414 of the cannulated body 404 is adapted to secure to a bone tap screw thread 416. The handle 402 further includes a guide wire locking mechanism, illustrated herein as a guide wire locking 418 which allows a user to lock or maintain a guide wire 420 in place, thereby preventing the guide wire 420 from rotational movement.

The use of a guide wire locking mechanism 418 offers several advantages during use in an operation. Guide wires are a common technique for placing cannulated bone screws into the pedicles of the spine. In this technique the surgeon will use a cannulated (i.e. a Jam Sheidi) instrument to identify and create the intended path for the screw to be placed. Once the path is created the surgeon will place a guide wire through the cannula and remove it leaving the guide wire behind as a guide for additional hole preparation instruments such as a drill and or bone tap and eventually bone screw. It is critical that the guide wire not be inadvertently advanced or removed during the entire preparation and screw insertion process. Typically, the surgeon will have an assistant manually hold the extension of wire protruding through the back of the instrument handle in an effort to control the position of the wire. This can present obstruction to the surgeon and is prone to human error. The guide wire management system 400 incorporates a guide wire locking mechanism in the handle which maintains the wire in position during the entire preparation and screw insertion process.

Figure 21:
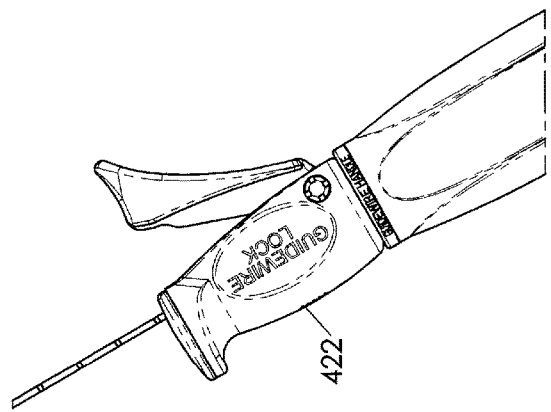
FIG. 21 illustrates the locking mechanism shown in FIG. 20.
Figure 23:
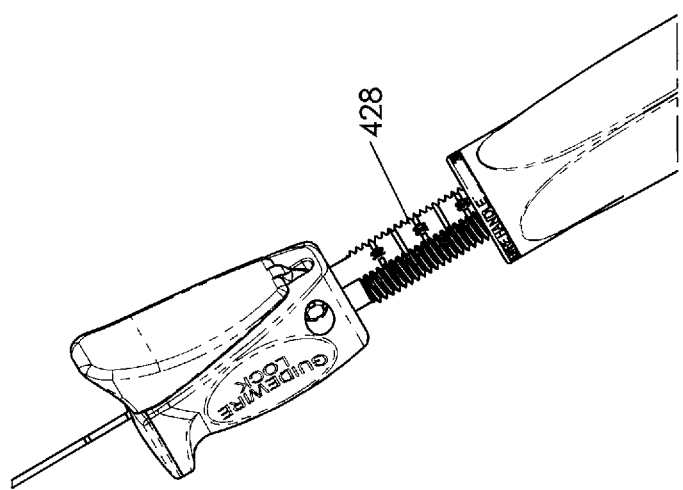
FIG. 23 illustrates an alternative view of the locking mechanism shown in FIG. 20.
Figure 22:
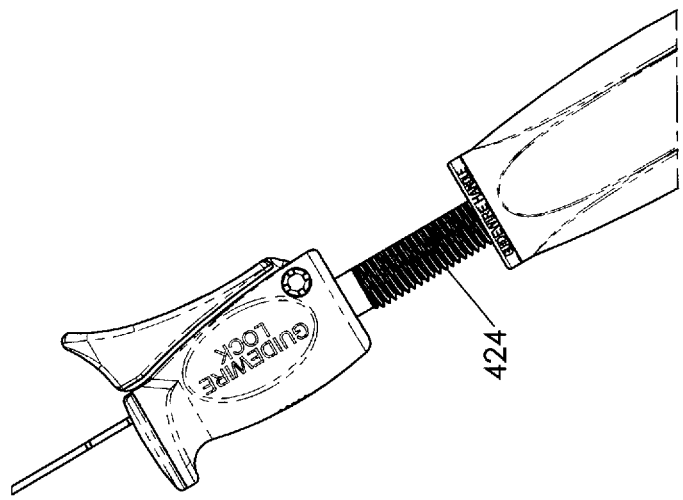
FIG. 22 illustrates an alternative view of the locking mechanism shown in FIG. 20.

Referring to FIGS. 21-23, an illustrative embodiment of the guide wire lock 418 is shown. The guide wire lock 418 contains an body 422 storing the internal locking mechanism, such as using a cam lock lever, for securing the guide wire 420 in place therein. A male threaded extension 424 extends from the body 422 and is used to communicate or couple with female threading 426 associated with the handle 402. Preferably, the threaded extension 424 has a thread pitch equal to that of the bone tap and bone screw pitch so when the cam locking mechanism is held stationary as the instrument handle 402 is advanced, the wire will maintain its position in space. The treaded extension 424 may also incorporate a scale, or positional markings 428 to identify the distance traveled from the starting position, thereby aiding the user in determining the depth of insertion during operation of the device.

Figure 24:
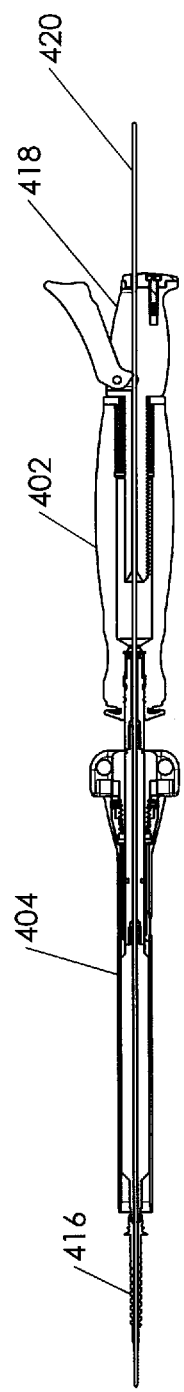
FIG. 24 is a cross sectional view of the guide wire management system.
Figure 25:
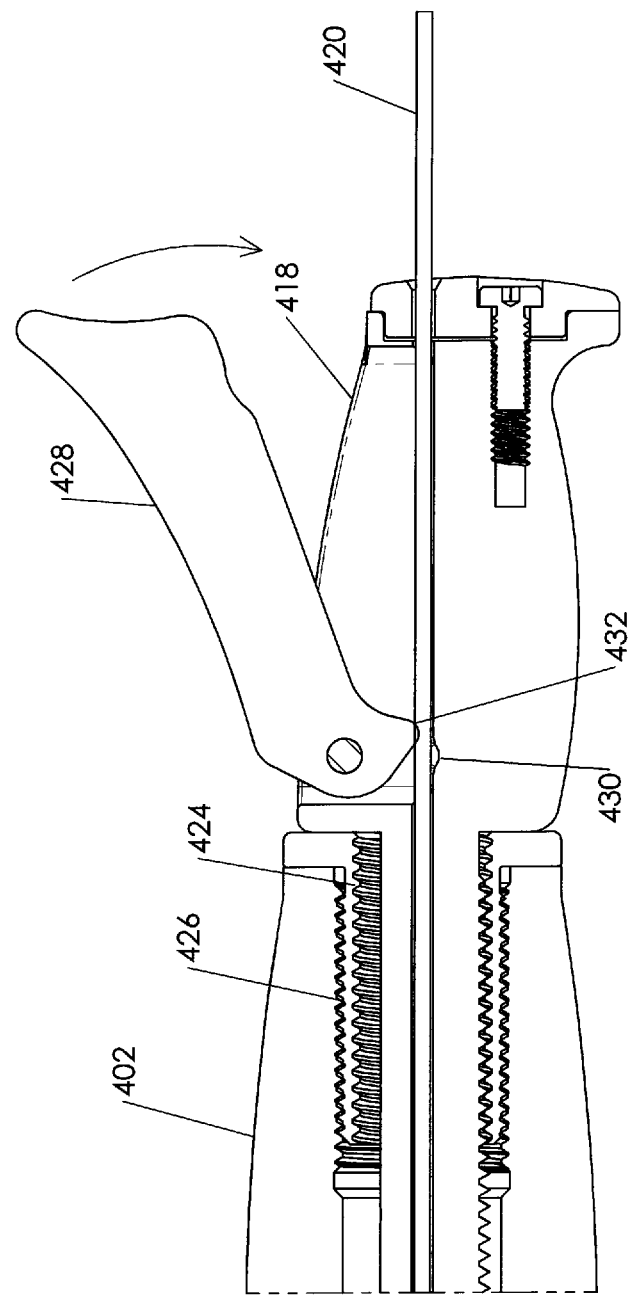
FIG. 25 is a cross sectional view of the guide wire lock in the open, non-locking position.
Figure 26:
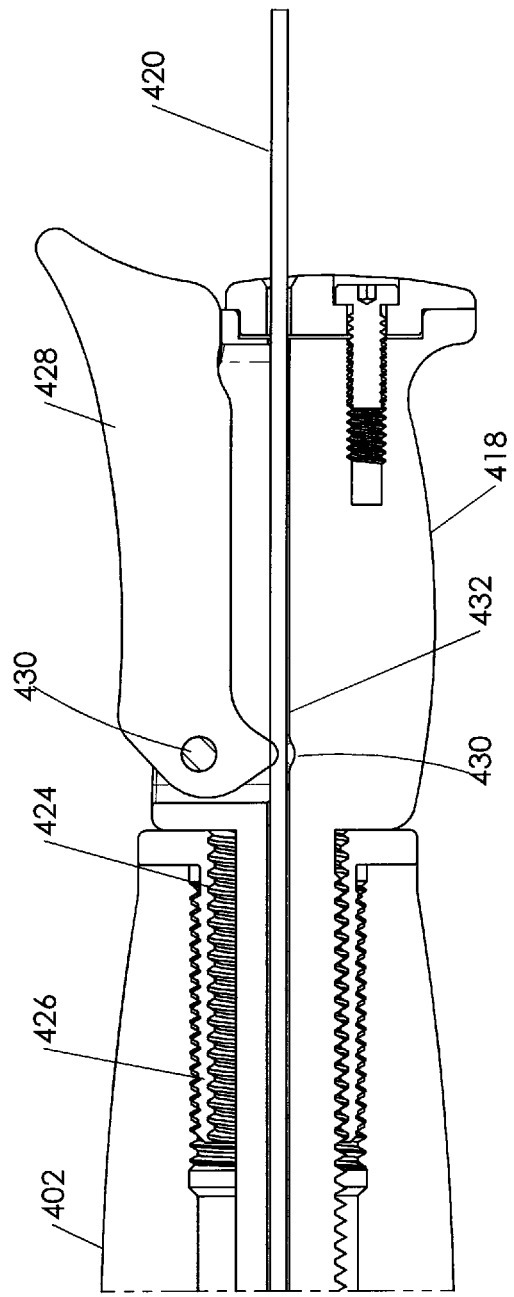
FIG. 26 is a cross sectional view of the guide wire lock in the closed, locked position.

FIGS. 24-26 are cross-sectional views of the guide wire management system 400, see FIG. 24, or the guide wire lock 418 in an open position, see FIG. 25 or closed position, see FIG. 26. The guide wire lock 418 comprises a cam lock lever 428 which rotates about pivot point upon manipulation a user. In the open position, i.e. the guide wire 420 is not locked in position, the guide wire is not engaged with a detent or recessed portion 430 positioned within the within the body 422. As a user actuates the cam lock lever 428, a cam 432 moves in a liner manner relative to the guide wire 420, pinching the portion of the guide wire 420 that overlays or rests above the detent or recessed portion 430 therein. In this position, the cam lock lever 428 maintains a portion of the guide wire within the detent or recessed portion 430 until released back to open position, preventing the guide wire 420 from rotational, or linear (i.e. movement along the longitudinal axis of the handle, locking it in place.

Figure 27:
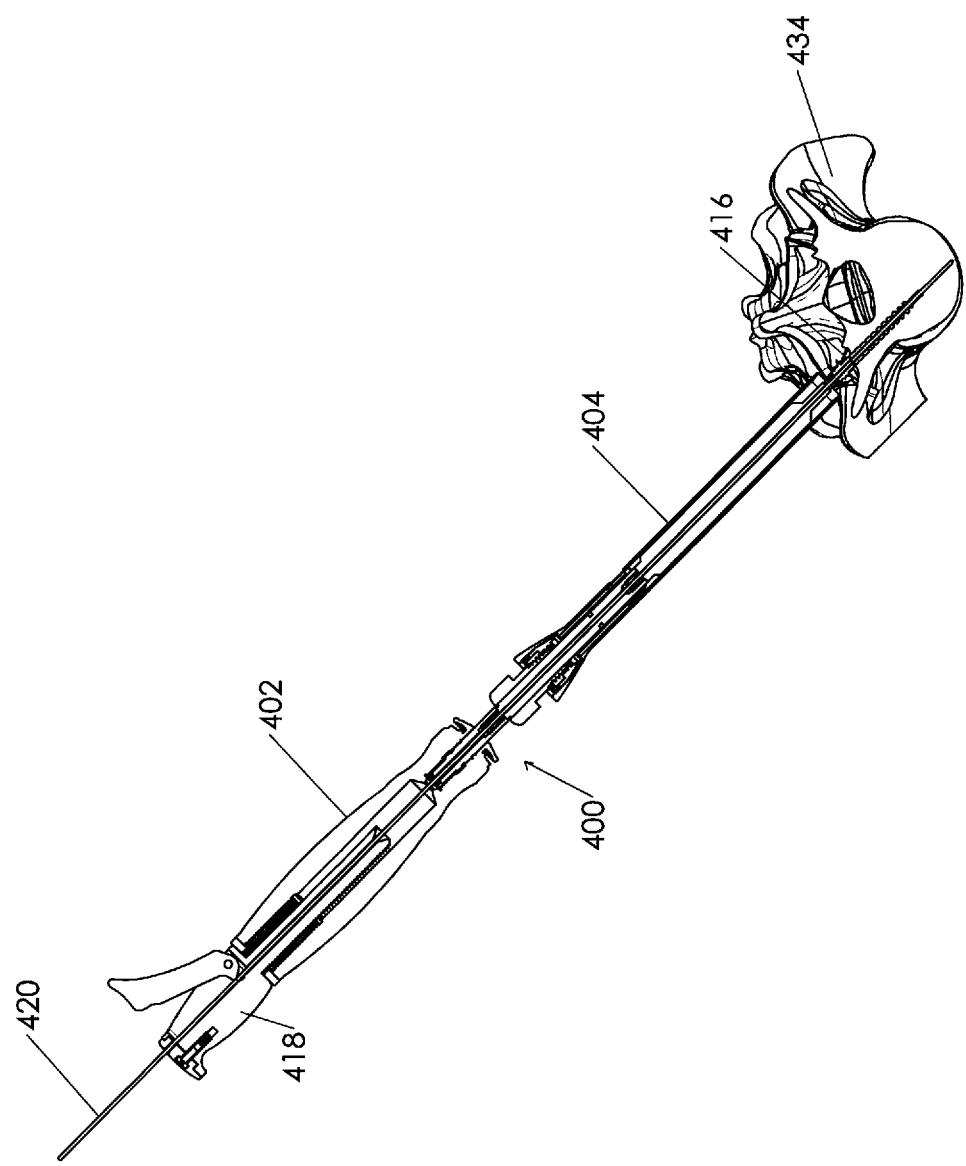
FIG. 27 illustrates the guide wire management system engaged with a vertebral body.

When inserted into a vertebral body 434, see FIGS. 27 and 28, the guide wire 420 can be held in the exact position by use of the guide wire lock 418. When the threaded extension 424 that engages an upper end of the handle 402, rotation of the handle 402 in relation to the guide wire lock 418 allows rotation of the bone tap screw thread 416 to have the exact same thread pitch movement. In this manner, rotation of the bone tap screw 416 is possible without movement of the guide wire 420. This device could be used during screw insertion and removal, tap insertion and removal to ensure the wire does not advance forward nor retreat back. The device could also be used to drive a wire forward in a controlled measurable manner.

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A guide wire tool comprising:
   a shank having an upper end and a lower end forming a length therebetween, said lower end including a bone tap screw thread formed along an outer surface of said shank and an end positioned awl, said shank including a central passageway extending along the length of said shank;
   a protective sleeve attached along a portion of the length of the lower end of said shank;
   a first handle attached to an upper portion of said shank;
   a guide wire capture handle, the first handle is slidable between said protective sleeve and said guide wire capture handle, said guide wire capture handle having a threaded rod operatively associated with said first handle and a locking member constructed and arranged to maintain a guided wire in stationary position wherein rotation of said handle allows rotation of said bone tap screw thread;
   a dialator positioned over a portion of said protective sleeve, said dialator slidably secured to a protective sleeve wherein said dialator expands upon the insertion of said sleeve and retracts to an original position upon withdrawal of said sleeve; and
   a guide wire extending through said guide wire capture handle through said end positioned awl;
   wherein said first handle is usable as a hammer or engaged with said bone tap screw for ease of rotation.

2. The guide wire tool according to claim 1 wherein said bone tap screw thread and said guide wire capture handle have the same thread pitch movement.

3. The guide wire tool according to claim 1 wherein said expandable dialator has a serrated end.

* * * * *